(12) United States Patent
Mitra

(10) Patent No.: US 8,190,245 B2
(45) Date of Patent: May 29, 2012

(54) OPTICAL TOMOGRAPHY SYSTEM USING SHORT-PULSE LASER FOR EARLY CANCER DIAGNOSTICS

(75) Inventor: Kunal Mitra, Satellite Beach, FL (US)

(73) Assignee: Florida Institute of Technology, Melbourne, FL (US)

( * ) Notice: Subject to any disclaimer, the term of this patent is extended or adjusted under 35 U.S.C. 154(b) by 0 days.

(21) Appl. No.: 13/086,769

(22) Filed: Apr. 14, 2011

(65) Prior Publication Data
US 2011/0208065 A1   Aug. 25, 2011

Related U.S. Application Data

(62) Division of application No. 11/693,955, filed on Mar. 30, 2007.

(51) Int. Cl.
*A61B 6/00* (2006.01)
(52) U.S. Cl. .......................... 600/476; 128/665
(58) Field of Classification Search ............. 600/476; 128/665
See application file for complete search history.

(56) References Cited

U.S. PATENT DOCUMENTS 5,348,018 A * 9/1994 Alfano et al. ............ 600/476
2007/0156037 A1 * 7/2007 Pilon et al. ............... 600/310

* cited by examiner

*Primary Examiner* — Brian Casler
*Assistant Examiner* — Saurel J Selkin
(74) *Attorney, Agent, or Firm* — Joel I. Rosenblatt

(57) ABSTRACT

Time-resolved optical tomography systems using a short pulse laser, may be used in detection and treatment of cancer and tumors. Information is conveyed about tissue interior by the temporal variation of the observed scattered, and reflected measured when short-pulse lasers interact with scattering-absorbing media like tissue. Multiple scattering-induced temporal signature that persists for time periods greater than the duration of the source pulse and is a function of the source pulse width, the scattering and absorbing properties of the medium, and the location in the medium where the properties undergo changes. If the detection is carried out on the same short time scale (comparable to the order of the pulse width), the signal continues to be observed even for long durations after the pulse has been off due to the time taken for the photons to migrate to the detector after multiple scattering in the tissue media.

1 Claim, 8 Drawing Sheets

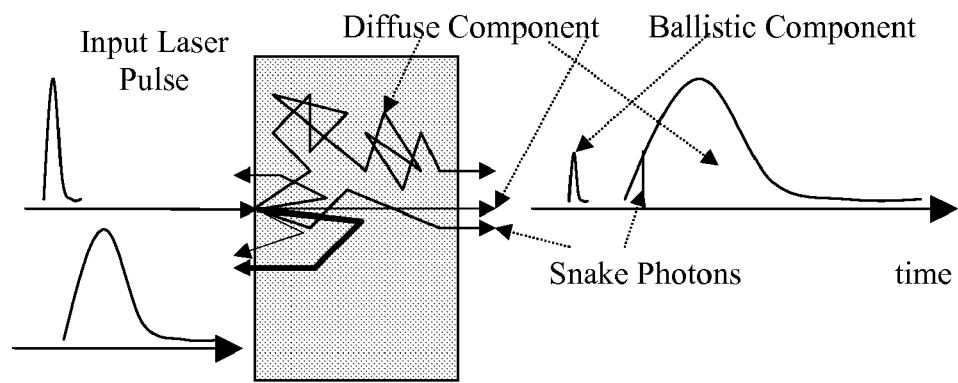
Figure 1
Figure 2aFigure 2b

| Breast Phantom | $k_a = 0.006$ mm$^{-1}$ | $k_s = 9.00$ mm$^{-1}$ |
|---|---|---|
| A | 1.1 x $k_a$ | 1.1 x $k_s$ |
| B | 2 x $k_a$ | 2 x $k_s$ |
| C | 3 x $k_a$ | 3 x $k_s$ |
| D | 4 x $k_a$ | 4 x $k_s$ |

OPTICAL TOMOGRAPHY SYSTEM USING SHORT-PULSE LASER FOR EARLY CANCER DIAGNOSTICS

CROSS-REFERENCE TO RELATED APPLICATION

This is a divisional application of U.S. application made under 35 U.S.C. 121 and claims the benefit under 35 USC §120 of U.S. patent application Ser. No. 11/693,955, filed Mar. 30, 2007.

FIELD OF THE INVENTION

The invention relates to methods of performing cancer diagnostic procedures, in particular diagnostic procedures for early cancer detection.

BACKGROUND OF THE INVENTION

Currently, different techniques are used for detection of tumors and other evidence of cancer. For example, cancerous tumors in the lungs are usually located by using conventional x-rays. X-ray mammography, the modality commonly used for breast cancer screening, cannot distinguish between malignant and benign tumors, and is less effective for younger women with dense, fibrous breasts. Moreover, their high energy can ionize the tissue and may be potentially harmful if used too often for routine screening or at high intensity. If a tumor is suspected from an x-ray image, a biopsy that requires invasive removal of tissue from the suspect region needs to be performed to determine if the tumor is benign or malignant. In some cases, cytology rather than excisional biopsy is performed. However, both of these diagnostic procedures require physical removal of specimens followed by tissue processing in the laboratory. As such, these procedures incur a relatively high cost because specimen handling is required and, more importantly, diagnostic information is not available in real time. Moreover, in the context of detecting early neoplastic changes, both excisional biopsy and cytology can have unacceptable false negative rates, often arising from sampling errors. Another technique, radioisotope imaging, exposes the body to radioactivity that is potentially harmful. Ultrasound lacks the resolution to detect objects with linear dimensions smaller than a few millimeters, and like x-rays, do not provide any information about tissue chemistry. MRI is a powerful technique with sub-millimeter spatial resolution but the cost of superconducting magnets needed for its operation makes it very expensive.

From the standpoint of detecting early cancer and tumors, a primary technological challenge arises from the fact that laser light is highly scattered in all directions by tissue. The nascent but rapidly developing technology of optical tomography using a short pulse laser holds the promise of providing non-invasively detailed information about the tissue interior by measuring the temporal profile of the time-varying transmitted and reflected optical signals. In optical tomography, a short pulse laser is focused on the region to be probed and the time-dependent scattered fluence rates are measured at different locations using ultrafast detectors. It is the intent of the method to obtain information about the interior of the tissue medium non-invasively from the time-resolved fluence or intensity measurements. Optical tomography is expected to yield physiological information with a safer, simpler and less expensive system than the other types of methods.

The problem of determining the optical properties of tissues and tumors and hence the state of the tissues from experimentally measured time-dependant laser intensity measurements then requires the development of software using sophisticated inverse algorithm based on transient radiative transport formulation. Optical tomography will thus provide information about cancer and tumor properties, location, and size with high resolution, which is critical for tumor necrosis. To achieve these goals, detailed experimental study of delivery of laser energy with high efficiency in tissue samples, phantoms, biochemical species, and animals such as rats and mice have been performed. Delivery of pulsed laser light to the cancerous cells and tumor is done using hollow waveguides having different coatings for high transmission efficiency.

There is a need for an optical tomography system using a short-pulse laser for cancer diagnostics.

BRIEF SUMMARY OF THE INVENTION

Time-resolved optical tomography systems using a short pulse laser according to the invention provides great advantage in detection and treatment of cancer and tumors, one of the leading causes of mortality in the U.S. and other parts of the world. By using a combination of a short-pulse light source and an ultrafast light detecting system, cancer and tumors can be detected in early stages prior to metastasis, when they are small, and hence can then be irradiated (killed) in situ.

This technology can be used for detection of tumors in tissue. In addition, it can be used for other applications, such as non-invasive detection of debonding in thermal tiles in a space shuttle.

An optical tomography system using a short-pulse laser source has distinct advantages over conventional systems using very large pulse width or cw lasers, at least in part due to the additional information conveyed about tissue interior by the temporal variation of the observed signal. When conventional cw laser sources are utilized, the information available is the magnitude of the net attenuation and the angular distribution of the transmitted or reflected signal. The scattered, reflected, and transmitted signals measured when short-pulse lasers interact with scattering-absorbing media like tissue possess a unique feature compared to the steady-state or cw laser measurements. The distinct feature is the multiple scattering-induced temporal signature that persists for time periods greater than the duration of the source pulse and is a function of the source pulse width, the scattering and absorbing properties of the medium, and the location in the medium where the properties undergo changes. If the detection is carried out on the same short time scale (comparable to the order of the pulse width), the signal continues to be observed even for long durations after the pulse has been off due to the time taken for the photons to migrate to the detector after multiple scattering in the tissue media.

There has recently been a strong interest in using lasers as diagnostic devices and therapeutic tomography is an example of short-pulse laser interaction with scattering-absorbing media such as biological tissue, which is of great scientific and engineering interest (Yamada, 1995; Yodh and Chance, 1995; Hebden and Wong, 1993; Berg et al., 1991; Jacques, 1989; Profio, 1989; Ishimaru, 1978a, b). The nascent field of optical tomography for medical imaging is made possible by a spectral window in the visible and infrared wavelength region where light absorption is very small and scattering dominates (Yamada, 1995; Yodh and Chance, 1995). Optical methods are a recent addition to the arsenal of non-invasive diagnostic tools available for the detection of disease, such as x-ray computed tomography, bronchoscopy, biopsies, magnetic resonance imaging, positron emission tomography, single photon emission computed tomography, ultrasound imaging, and electrical impedance tomography.

Time-resolved optical tomography is a novel biomedical imaging technology by which one can detect small tumors in tissue in earlier stages normally not detected by other techniques. Optical technologies have the potential capability of performing in situ diagnosis on tissue without the need for sample excision and processing. This diagnostic information can be available in real time. In addition, since removal of tissue is not required for optical diagnostics, a more complete examination of the organ of interest can be achieved than with excisional biopsy or cytology. The experimental techniques will aid in predicting how the measured temporal radiation signal changes with property distributions. Optical tomography using a short-pulse laser will provide detailed morphological and physiological information about the state of the tissue without any adverse side effects associated with some of the techniques mentioned above.

BRIEF DESCRIPTION OF THE DRAWINGS

FIG. 1 is a diagram showing photon propagation in a random medium.

FIG. 2a is a diagram showing the experimental far-field intensity distribution corresponding to multimode input laser emission.

FIG. 2b is a diagram showing the experimental far-field intensity distribution corresponding to the laser beam output of the hollow taper.

DETAILED DESCRIPTION OF THE INVENTION

Figure 3:
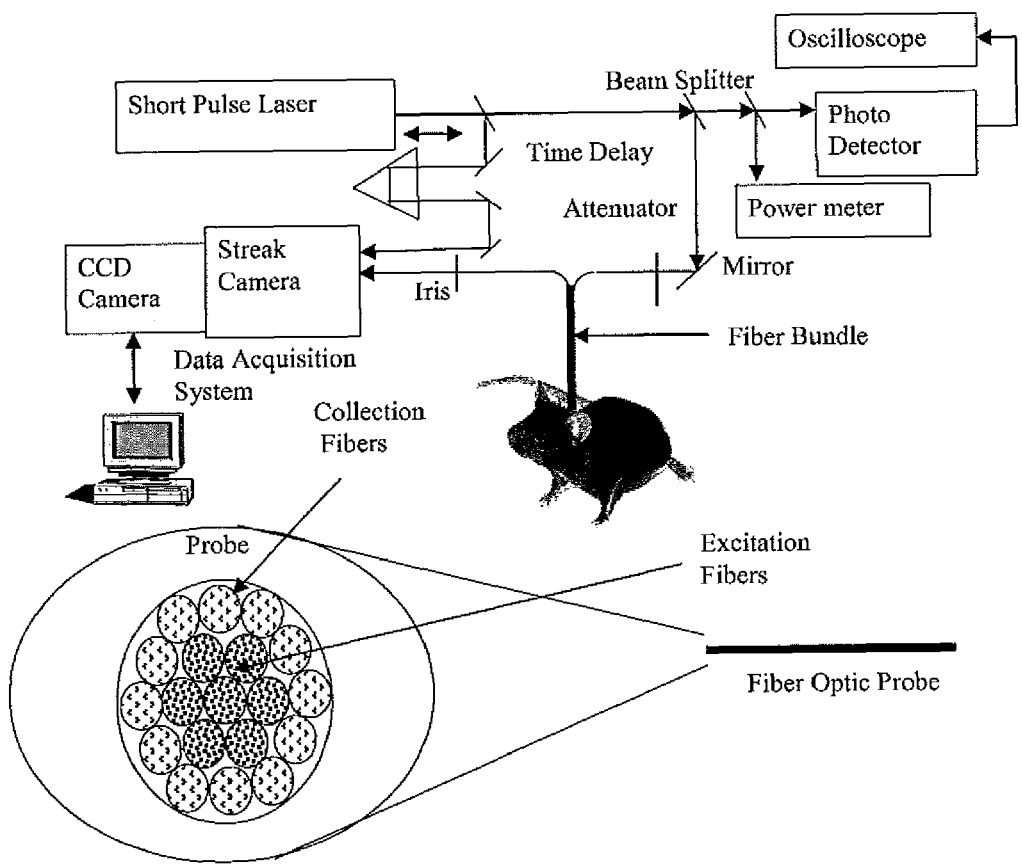
FIG. 3 is a schematic diagram of the experimental setup used for phantom and animal studies.

The invention is an optical tomography system for detection of early tumors and cancer using time-resolved intensity measurements. The location, size, and optical properties of tumors are determined from measured temporal reflected and transmitted signals. Coupling and delivery studies of short-pulse laser energy into tissue using hollow waveguides and tapers have been developed. Software based on transient radiative transport models is used for reconstructing the images from measured reflected and transmitted signals.

A short-pulse laser system is used for detection of tumors in tissue. Steps to further the development and understanding of time-resolved optical tomography for biomedical imaging include determination of optical properties of tissue medium, validation of experimental data using numerical models, better understanding of short-pulse laser transport processes, and gaining insight about laser-tissue interaction characteristics via careful experimentation. Transient radiative transport models are used for analyzing ultra-short laser pulse propagation through scattering media such as tissue and ocean water, short-pulse lasers are used as a remote sensing tool in probing the characteristics of random scattering media, and benchmark solutions are developed by identifying the research needs in the transient radiative transport area (Sakami et al., 2002a, 2002b; Mitra and Kumar, 1999; Mitra and Churnside, 1999; Kumar and Mitra, 1999).

When photons travel through any turbid medium, three signal components can be defined, namely, the ballistic component, the diffusive component, and the snake component. The coherently scattered or ballistic photons propagate in the direction of the incoming beam, traverse the shortest path, retain most of the characteristics of the incident photons, and carry the maximum information about the interior structure of the scattering medium. The ballistic photons, though they carry the maximum information, are not efficient for probing a thick medium, as very few ballistic photons come out of a thick medium. The photons that suffer multiple scattering travel long distances within the medium, and lose many of their initial characteristics, but also carry information about the structure inside the medium and emerge later in all directions. They constitute what is known as the diffusive component of the transmitted light. The photons that scatter slightly in the forward direction retain significant initial properties and information on structure hidden in the scattering medium. These photons are called snake photons because their trajectories resemble a wriggling snake. Since the photons of incident short light pulse spend different times in transit through the intervening medium, the transmitted pulse as well as the reflected pulse becomes broadened, with the ballistic photons arriving first followed by the diffusive and snake photons. The relative intensity of the three components in the reflected signal as well as the transmitted signal is a function of the wavelength and pulse width of the incident pulse and of the characteristics of the medium being probed.

Experimental Measurement Technique

The diffusive component of the transmitted light is an interesting aspect of the invention. The diffusive photons are the ones that suffer the most scattering. Multiple scattering-based temporal signatures persist for a time period greater than the source pulse. Again the use of diffusive photons enables detection to be carried out on the same short time scale (comparable to the pulse width), and hence the signal continues to be observed even for long durations after the pulse has been off due to the time taken for the photons to migrate to the detector after undergoing multiple scattering in the media. The use of diffusive photons also enables the probing of thicker media, unlike techniques like time gating, which uses the ballistic components to reconstruct the image of the tissue interior.

Before conducting in vivo experiments on animals to detect tumors present in them, it is important to test and characterize the detection scheme by performing experiments on tissue phantoms. For delivery of laser energy to the cancerous cells it is preferable that the short-pulse laser output is optimized. The use of hollow waveguides and tapered non-imaging optical elements opens the possibility of delivering laser energy with high efficiency into lung tissues. To feed the laser beam into the fiber, various focusing elements such as lenses and objectives are conventionally used. However these focusing elements introduce additional absorption, Fresnel reflection losses, and aberrations. They also lead to fiber damage because of sharp focusing and have significant alignment problems. As an alternative means, optical fiber tapers and hollow waveguides are extensively used for matching and delivering laser emission.

FIG. 2 shows the experimental far-field intensity distribution corresponding to (a) the infrared laser input emission and (b) the laser beam output at the hollow uncoated glass taper. As clearly seen in FIG. 2(a), the profile contains random fluctuations and many small energy peaks that correspond exactly to the strongly multimode structure of the input laser emission. When such a multimode laser beam is introduced into the taper, an excellent smooth distribution, nearly a perfect Gaussian profile, is observed as shown in FIG. 2(b). The formation of this smooth beam profile can be attributed to the mutual action of the following factors: (i) the direct parallel laser excitation that provides the most appropriate conditions (a minimum input angle) for grazing incidence reflection in the taper; (ii) the mode coupling process that is caused by the taper core variations and leads to redistribution of the optical power among the guided local normal modes in the taper and to formation of an upward power flow produced by the mode conversion of lower-order to higher-order modes; and (iii) the taper filtering effect that decreases the amplitudes of the high-order guided local normal modes. This laser output can be propagated down a hollow waveguide with the least chance of damage and with high transmission efficiency.

Figure 4:
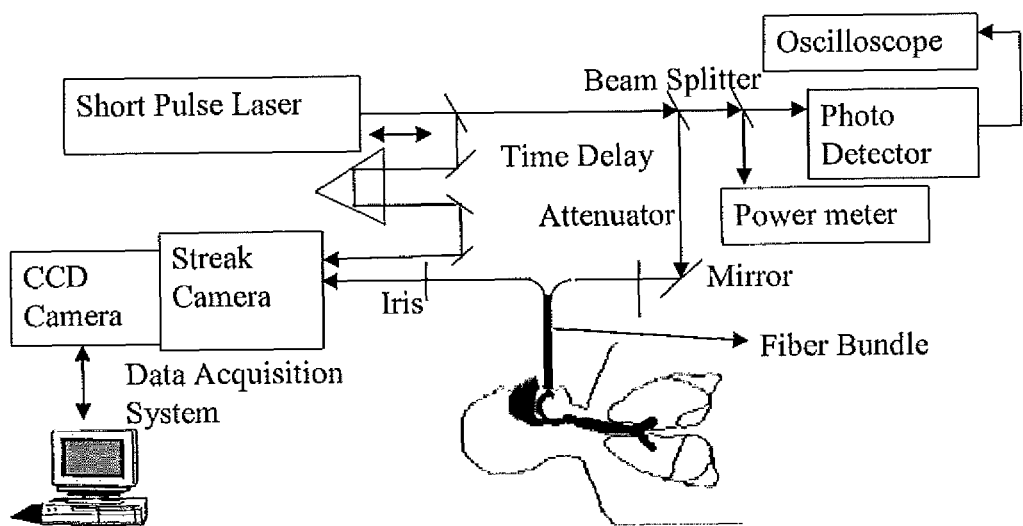
FIG. 4 is a schematic diagram of the experimental setup used for human studies.
Figure 5:
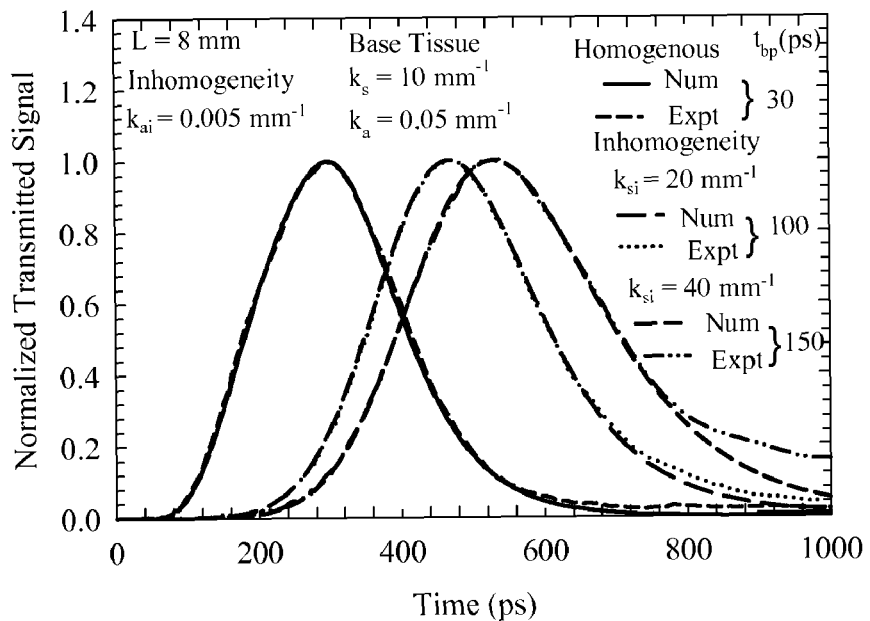
FIG. 5 is a diagram showing a comparison of transmitted signals between a homogeneous tissue phantom and a tissue phantom including an inhomogeneity for different scattering coefficients.
Figure 6:
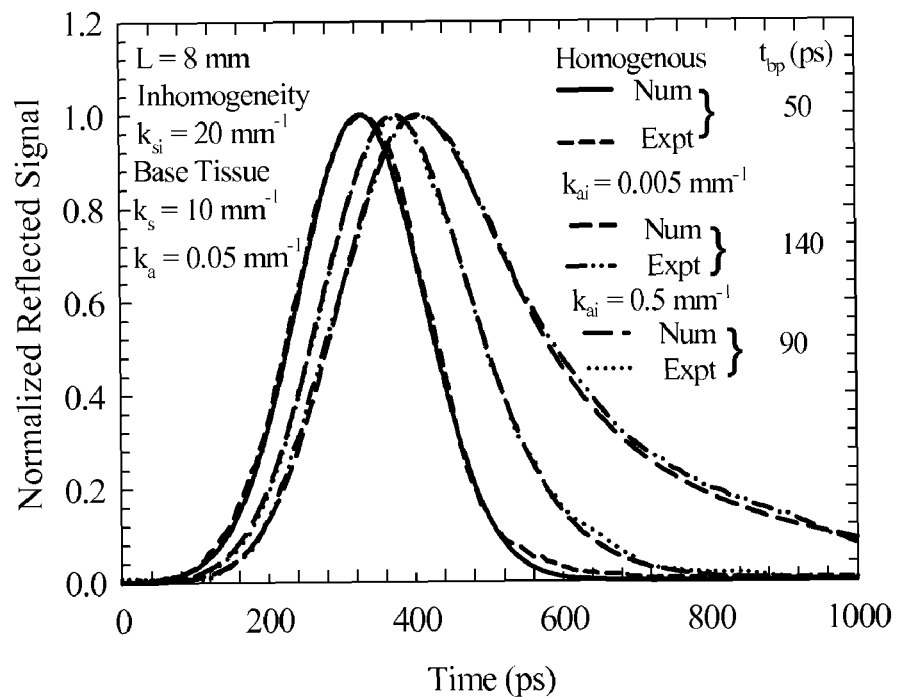
FIG. 6 is a diagram showing a comparison of reflected signals between a homogeneous tissue phantom and a tissue phantom including an inhomogeneity for different absorption coefficients.

A schematic of the experimental setup currently used for generating preliminary data on phantoms and on animals is shown in FIG. 3. FIG. 4 shows the schematic of the setup to be used with human being for an application such as lung cancer detection. In FIG. 5 the normalized transmitted signals are compared between that of a homogenous tissue phantom and that of a phantom containing an inhomogeneity having different scattering coefficients. For the homogenous tissue phantom the scattering coefficients and absorption coefficient are 10 mm$^{-1}$ and 0.05 mm$^{-1}$, respectively. The thickness (L) of the tissue phantoms for all the cases is 8 mm. For the tissue phantom containing the inhomogeneity, the optical properties of the base tissue phantom are same as the homogenous phantom while the scattering coefficients of the inhomogeneity are 20 mm$^{-1}$ and 40 mm$^{-1}$. The absorption coefficient of the inhomogeneity is kept the same and is equal to 0.005 mm$^{-1}$. There is a very good agreement between numerical modeling results and experimental measurements with a little separation in the tail section. This separation can be attributed to the fact that as the scattering coefficient is increased, the photons suffer random scattering and persist inside the medium for a longer time, resulting in very few photons leaving the medium and thus contributing to the noise. Further normalization of the signal also amplifies the noise at the tail of the pulse. The transmitted signal values in the case of the homogenous tissue phantom are zero over the time that the photons take to traverse the phantom thickness. It is observed that with the increase in the scattering coefficient of the inhomogeneity, the temporal broadening of the pulse ($t_{bp}$) from the tissue phantom containing the inhomogeneity increases. A higher scattering coefficient increases the optical depth of the medium and as a result the transmitted photons take a longer time to reach the detector. This is manifested in the higher temporal broadening of the transmitted pulse. FIG. 6 shows the comparison of the normalized reflected intensities between a homogenous tissue phantom and the tissue phantom containing the inhomogeneity for different absorption coefficients of the inhomogeneity. The scattering coefficient of the inhomogeneity is kept constant at 15 mm$^{-1}$ while the absorption coefficients of the inhomogeneities are taken as 0.5 and 0.005 mm$^{-1}$. With the increase in the absorption coefficient of the inhomogeneity, greater numbers of photons are absorbed. This result in greater attenuation of the incident light and as a result the total temporal broadening of the reflected pulse reduces with the increase in the absorption coefficient.

Figure 7:
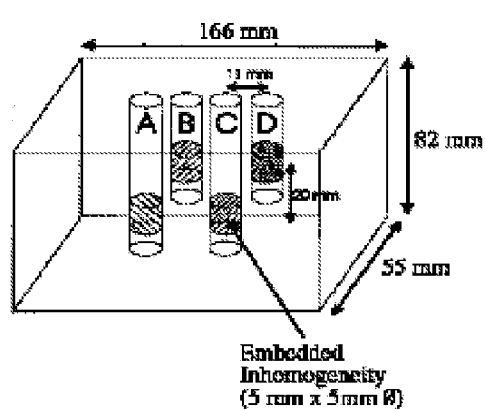
FIG. 7 is a diagram showing a breast phantom including an inhomogeneity having different scattering and absorption coefficients than does the base tissue.
Figure 8A:
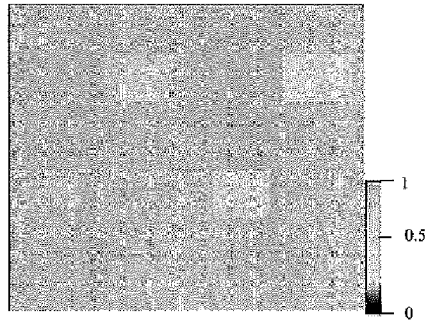
FIG. 8a is a diagram showing absorbing contrast phantoms.
Figure 8B:
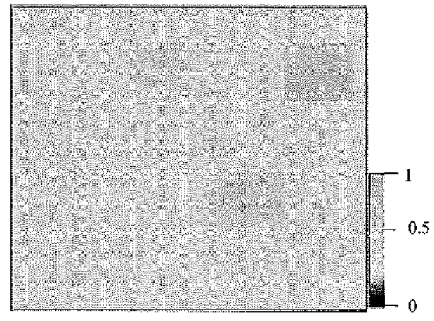
FIG. 8b is a diagram showing scattering contrast phantoms showing the locations of the inhomogeneities.

Two tissue-like plastic phantoms are considered, each containing four small embedded objects. In one phantom these objects had a range of scattering coefficients, and in the other a range of absorption coefficients. The optical properties of each slab corresponded to $k_a$=0.006 mm$^{-1}$ and $k_s$=9 mm$^{-1}$, which fall within the reported range of values for healthy breast tissue. Each slab had a refractive index of 1.56 and dimensions of 55 mm×82 mm×166 mm. Four cylinders were manufactured with the same absorption as the slab, but with scatter coefficients of 4, 2, 1.5, and 1.1 times greater than the slab, and another four were manufactured with the same scatter coefficient as the slab, but with different absorption coefficients varying in the same ratios. Each cylinder had a length of 5 mm and a diameter of 5 mm. The schematic of the phantom is shown in FIG. 7. A line scan was performed which involved translating the fiber optic probe 50 mm horizontally and 40 mm vertically in 2-mm steps, with the center of the scan corresponding to the center of the phantom, and the time-resolved optical signals were recorded at each location. The reflected intensities from the scattering contrast phantom and absorption contrast phantom are used to obtain a time-resolved image of the tissue phantom as shown in FIG. 8(a) and FIG. 8(b). The cylinder with the highest absorption or scattering coefficient is easily visible while the ability to identify the other cylinders decreases with the reduction in absorption or scattering coefficient. It was apparent in some of the time-resolved images that the observed positions of some cylinders did not always correspond exactly with their expected positions on the tissue phantoms. A possible reason might be that due to the physical constraints of the measurement technique, it was not possible to scan the data at smaller intervals. Also due to the presence of the multiple inhomogeneities, the contrast between the inhomogeneities is not very evident.

Experiments are performed on albino Wistar rats with tumorogenic materials applied over the skin and also injected below the skin surface. Before the tumorogenic materials are applied, the rats are anaesthetized using ketamine hydrochloride as the drug.

The dosage is 150 mg/kg of body weight. A mixture of India ink and Titanium dioxide is used to simulate the tumor. 4 ml of India ink is mixed with 0.1 gm of TiO2. 50 IA of the mixture is applied to skin surface as well as injected below the skin surface. The tumor diameter is around 2 mm. For the case of the tumor injected below the surface, the depth at which the tumorogenic agents are injected is unknown and the goal is to detect the location and depth of the tumor using time-resolved measurement techniques. India ink is used since it is a highly absorbing media and its absorption properties are well characterized at 514 nm, while TiO2 is highly scattering and is also potentially carcinogenic. It has been observed from literature that the tumors have absorption and scattering coefficients different from the base tissue and thus a combination of scattering absorbing media was used to simulate the tumor.

After the completion of the experiments, rats are allowed to recover to a healthy state and then returned to the university's animal care facility. All experimental procedures on rats and mice are approved by Florida Tech's Institutional Animal Care and Use Committee (IACUC).

Figure 9A:
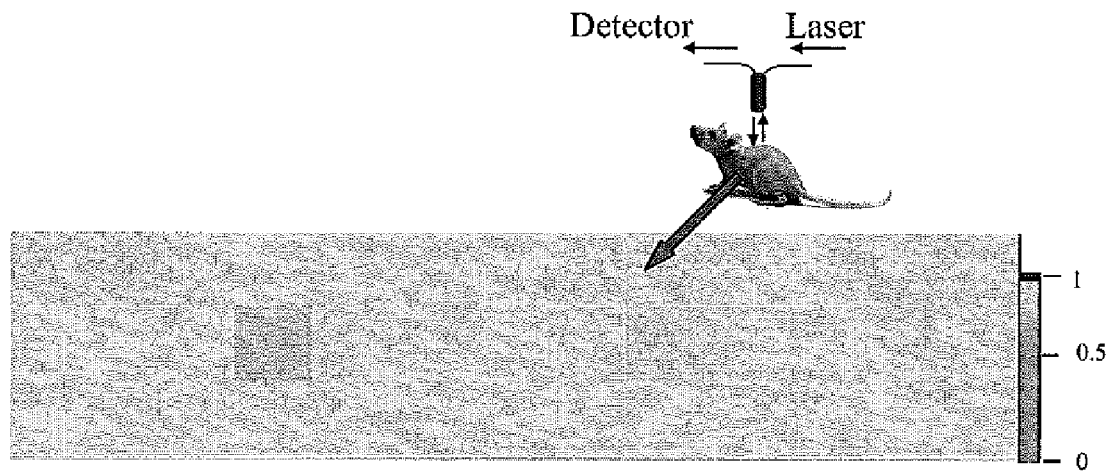
FIG. 9a is a diagram showing the pixel distribution of the reflected intensities for a rat with no tumor.
Figure 9B:
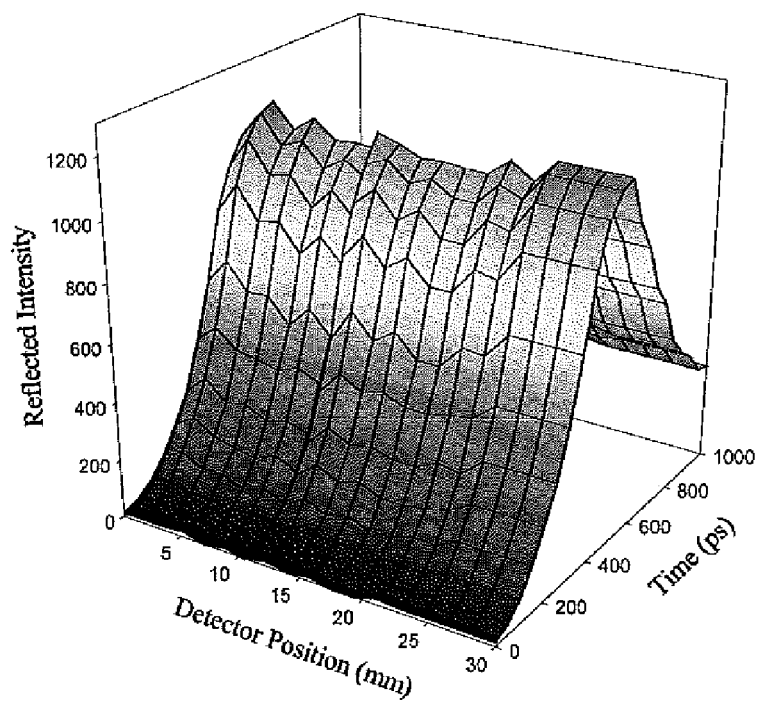
FIG. 9b is a diagram showing the three-dimensional distribution of the reflected intensity for a rat with no tumor.
Figure 10A:
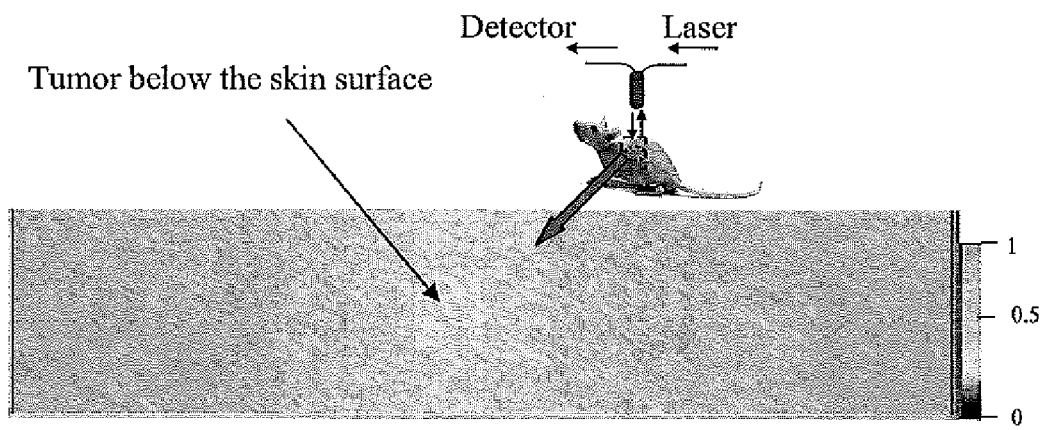
FIG. 10a is a diagram showing the pixel distribution of the reflected intensities for a rat with a tumor injected below the skin surface.
Figure 10B:
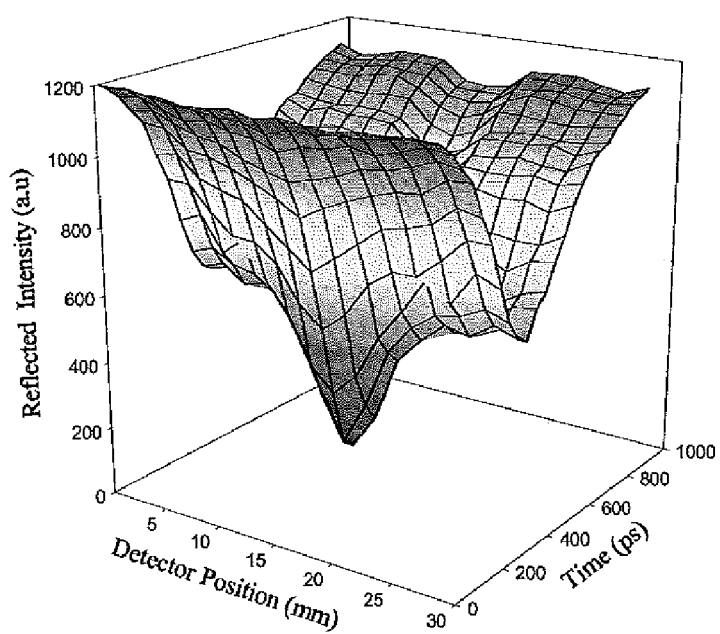
FIG. 10b is a diagram showing the three-dimensional distribution of the reflected intensity for a rat with a tumor injected below the skin surface.
Figure 11A:
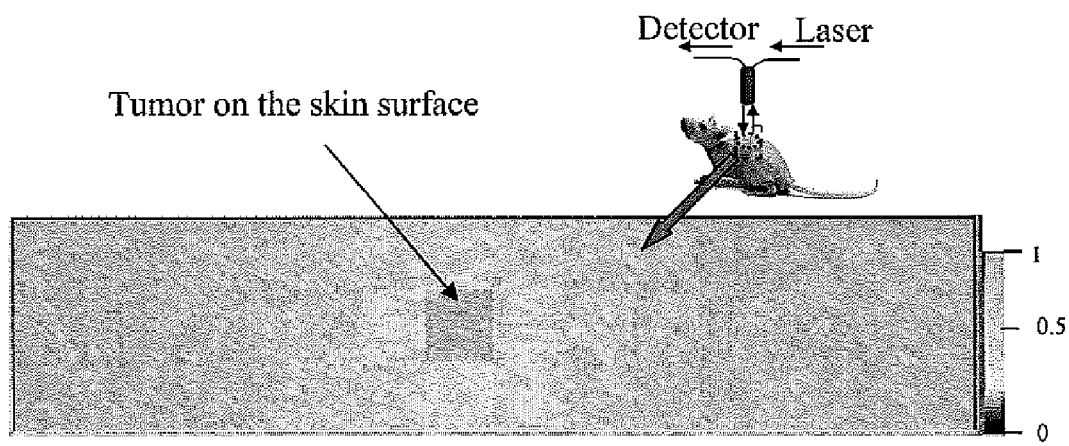
FIG. 11a is a diagram showing the pixel distribution of the reflected intensities for a rat with a tumor on the skin surface.
Figure 11B:
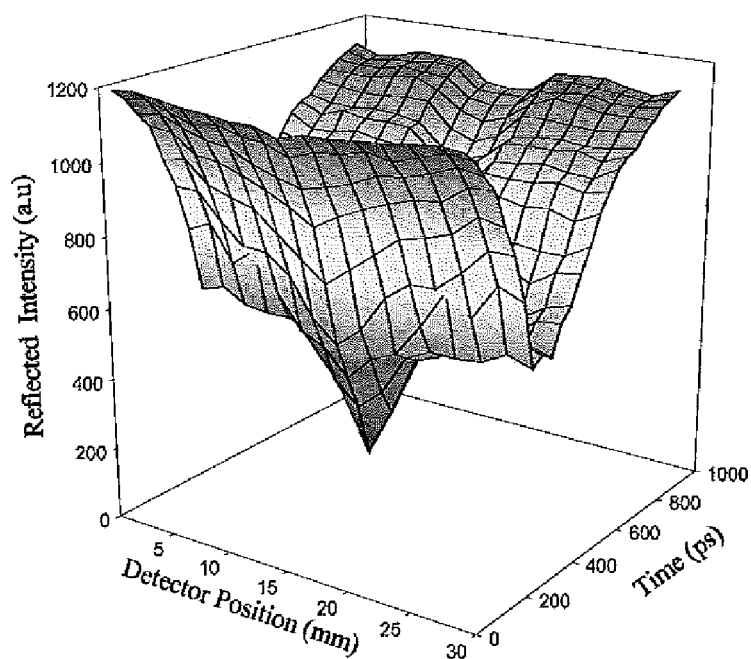
FIG. 11b. is a diagram showing the three-dimensional distribution of the reflected intensity for a rat with a tumor on the skin surface.

A complete understanding of the tumor size and location can be obtained by the pixel representation of the reflected intensities as shown in FIGS. 9 (a), 10 (a) and 11 (a). A total area of 30 mm×6 mm on the rat body containing the tumor was scanned and the reflected optical signals were collected at intervals of 2 mm. Finer resolution for the scanning was not possible since it would have required a lot of time and there was a danger of the anaesthetized rat getting active and thus disturbing the experiment. The reflected intensities are normalized with respect to their peak values and a pixel distribution of the intensities was obtained on a scale from 0 to 1. A pixel value of 0 implies that the entire incident light is absorbed while a pixel value of 1 implies that the entire incident light is reflected. FIGS. 9 (b), 10 (b) and 11 (b) demonstrate the corresponding 3-dimensional reflected intensities obtained by scanning from rats with materials applied to the skin surface as well as injected below the surface. It is observed from the plots that the reflected signals from the rats are nearly the same except near the location of the tumor. The reflected intensity is higher from the tumor that is injected below the skin surface than from the tumor that is on the skin surface. Tumor models have higher absorption coefficient than surrounding healthy tissue. Therefore, for the case of materials injected on the surface, a majority of the photons are absorbed.

However, for the material injected below the surface, a majority of the photons are reflected from the skin surface and a few reach the site of injection. As a result, the number of photons reaching the detector from material located below the skin is less compared to the case when the material is applied to the surface.

Figure 12:
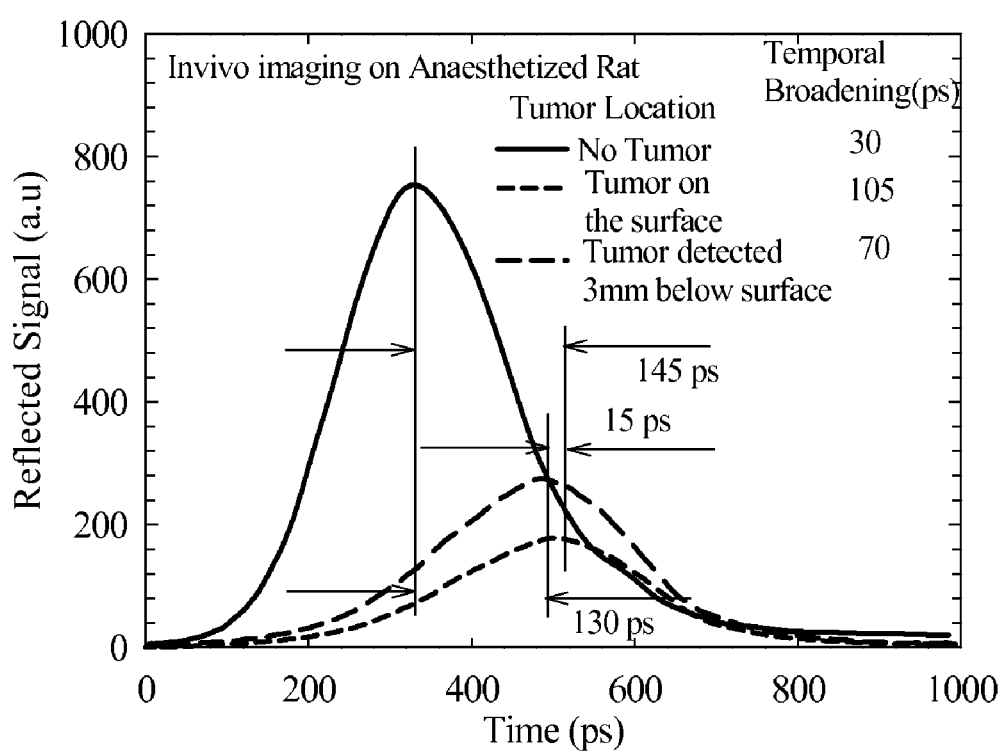
FIG. 12 is a diagram showing the comparison of the temporal reflected intensities for different tumor locations.

It is observed from FIG. 12 that the reflected intensity is highest for a rat with no tumor model injected since the model has a higher absorption than the healthy tissue and therefore attenuates the reflected signal. The key feature in this figure is the delay of 15 ps between the reflected signals from a tumor located below the skin and from a tumor located on the skin surface. 15 ps is the additional time taken by the reflected photons from the tumor on the surface to reach the detector compared to the photons reflected from the tumor located below the skin surface. With the tumor model on the skin, a majority of the photons are absorbed and very few are reflected while for a tumor below the skin surface most of the photons are reflected from the skin surface and very few reach the tumor model location that are absorbed. The speed of light inside the tissue is $1.95 \times 10^8$ m/s. Multiplying the peak separation time between the reflected signals by the speed of light in tissue gives the depth of the tumor model as 15 ps×$1.95 \times 10^8$ m/s=2.95 mm. Thus, using this technique we can obtain a quantitative idea of the depth at which tissue inhomogeneities are located below the skin surface.

Software Development

In optical tomography experiments, the measured transmitted/reflected signals collected using a streak camera needs to be validated using the radiant transport. The transient radiative transfer equation for laser propagation through tissue can be written as (Modest, 1993; Brewster, 1992; Siegel and Howell, 1992)

$$\frac{l}{c}\frac{\partial I(\vec{r}, \hat{s}, t)}{\partial t} + \hat{s} \cdot \vec{\nabla} I(\vec{r}, \hat{s}, t) = -k_e I(\vec{r}, \hat{s}, t) + \frac{k_s}{4\pi}\int_{4\pi} I(\vec{r}, \hat{s}', t)\Phi(\hat{s}' \to \hat{s})d\Omega' + S(\vec{r}, \hat{s}, t)$$

where l is the intensity, c is the speed of light in the medium, t is the time, k is the radiative coefficient (subscripts e, s, and a refer to extinction, scattering, absorption, respectively), $\hat{s}$ is the unit vector in the direction of intensity, $\Omega'$ is the solid angle around $\hat{s}'$, $\vec{r}$ is the spatial location, S is the incident radiation source term, and $\Phi$ is the scattering phase function.

The above is an integro-differential equation where the partial differentials correspond to a hyperbolic differential equation, which yields a wave solution. The equation of transfer is complicated because of the integral on the right side corresponding to the in-scattering gain term. Different numerical techniques to be used to solve the above transport equation are the spherical harmonics expansion, discrete ordinates, direct numerical integration, and Monte Carlo simulation. Detailed discussion of the merits and demerits of different methods and solution methodology is not provided here and can be found in the literature (Sakami et al, 2002a, 2002b; Sawetprawichkul et al., 2002, 2000; Mitra and Kumar, 1999; Kumar and Mitra, 1999; Yamada, 1995).

After the validation of the forward problem with the experimental measurements, the inversion algorithm is developed. The software is capable of taking as an input the measured reflection and transmission data and obtaining the optical properties of the medium using an inversion algorithm. The fundamental procedure is as follows: (1) set up an initial grid and estimate distributions of the scattering and absorption coefficients in the medium; (2) conduct the forward reconstruction by the hyperbolic transient models incorporating the distributions of the optical properties; (3) compare forward results with measured data, (4) if they are in agreement then stop and the assumed distributions of the optical properties are the solutions of the inverse problem; else renew the distribution of optical properties by an error norm or residual minimization algorithm; (5) update grids using new distributions to achieve computational efficiency; (6) go back to step (2) and processes (2) to (5) are repeated until the convergence is reached.

An adaptive grid generation technique will be used which generates a grid automatically for a given shape and modifies it during the solution procedure based on modification criterion selected for computational accuracy and efficiency (Zhang and Moallemi, 1995). This is accomplished by automatically examining the numerical solution at every step and increasing the size of the grids in regions where the properties are uniform and refining the size (increasing the resolution) in regions where properties are varying. The computational method for solving the forward problem then involves mapping the complex grids to a square computational domain (Yang, 1992), which is then solved by the transient radiative transport models.

The invention claimed is:

1. A system for detecting the depth of non homogeneities in a body, using time resolved optical tomography, comprising, a computer data processor; said computer data processor including a memory, a computer program operating said computer data processor, a data base, a data base program, a light detector, and a display;

a scanning short pulse light source producing a light pulse with a light pulse intensity with a light pulse width and light pulse time period, and transmitting said light pulse to a body containing a tumor on the surface of a body and a tumor below the surface of a body;

said computer data processor, connected to said light source and to said light detector, responsive to said computer program, recording in said data base, or producing on said display, the intensity of reflected light scattered for separate intervals on a body from a tumor on the surface of said body and the intensity of said reflected light scattered for separate intervals on a body from a tumor below the surface of said body;

said computer data processor, responsive to said computer program and said recording of said intensity of said reflected light scattered for separate intervals on a body from a tumor on the surface of a body and said recording of said intensity of said reflected light scattered for separate intervals on a body from a tumor below the surface of a body, recording the additional time for said intensity of said reflected light scattered from a tumor on the surface of a body to reach the light detector, compared to the time taken for said reflected light scattered from a tumor below the surface of a body, to reach said light detector;

said computer data processor responsive to said computer program, and to said recording of additional time, multiplying the peak separation time between said additional time for said reflected light scattered from a tumor on the surface of a body to reach said light detector, compared to said time taken for said reflected light scattered from a tumor below the surface of a body to reach said light detector, by the speed of light and recording the result of said multiplying; and said computer data processor responsive to said computer program, displaying or recording said result of said multiplying as a quantitative measurement of the depth of a tumor below said surface of a body.

* * * * *